United States Patent [19]
Förster et al.

[11] Patent Number: 5,858,922
[45] Date of Patent: Jan. 12, 1999

[54] HERBICIDAL FLUOROTHIADIAZOLYL OXYACETAMIDES

[75] Inventors: Heinz Förster, Kadenbach; Achim Bertsch, Köln; Stefan Böhm, Krefeld; Hans-Joachim Diehr, Wuppertal; Ernst Kysela, Bergisch Gladbach; Markus Dollinger, Leverkusen; Hans-Joachim Santel, Leverkusen, all of Germany

[73] Assignee: Bayer Aktiengesellschaft, Leverkusen, Germany

[21] Appl. No.: 913,075

[22] PCT Filed: Mar. 1, 1996

[86] PCT No.: PCT/EP96/00836

§ 371 Date: Sep. 5, 1997

§ 102(e) Date: Sep. 5, 1997

[87] PCT Pub. No.: WO96/28434

PCT Pub. Date: Sep. 19, 1996

[30] Foreign Application Priority Data

Mar. 14, 1995 [DE] Germany .................. 195 09 044.6

[51] Int. Cl.⁶ .................. A01N 43/82; C07D 285/13
[52] U.S. Cl. .................. 504/219; 504/167; 504/170; 504/262; 504/287; 504/290; 548/134; 548/136
[58] Field of Search ................. 548/136, 134; 504/219, 167, 170, 262, 287, 290

[56] References Cited

U.S. PATENT DOCUMENTS 5,096,483  3/1992  Forster et al. .................. 71/90

FOREIGN PATENT DOCUMENTS 0 192 117  8/1986  European Pat. Off. .
0 300 344  1/1989  European Pat. Off. .

OTHER PUBLICATIONS

C.A. 111:39374k, vol. 111 (1989) p. 603 (Abstract).

*Primary Examiner*—Johann Richter
*Assistant Examiner*—Ebenezier Sackey
*Attorney, Agent, or Firm*—Sprung Kramer Schaefer & Briscoe

[57] ABSTRACT

The invention relates to novel fluorothiadiazolyloxyacetamides of the formula (I)

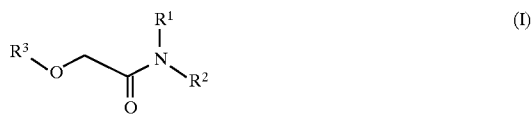

in which

R¹ represents hydrogen or respectively optionally substituted alkyl, alkenyl, alkynyl or arylalkyl, R² represents respectively optionally substituted alkyl, alkoxy, alkenyl, alkenyloxy, alkynyl, cycloalkyl, cycloalkenyl, aryl, arylalkyl or arylalkyloxy, or R¹ and R² together with the nitrogen atom that they are attached to form an optionally substituted saturated or unsaturated nitrogen heterocycle which may contain further hetero atoms and to which a benzo grouping may be fused, and R³ represents fluorothiadiazolyl, to a process and to novel intermediates for their preparation and to their use as herbicides.

4 Claims, No Drawings

HERBICIDAL FLUOROTHIADIAZOLYL OXYACETAMIDES

This application is a 371 of PCT/EP96/00836 filed on Mar. 1, 1996.

The invention relates to novel fluorothiadiazolyloxyacetamides, to a process and novel intermediates for their preparation and to their use as herbicides.

It is already known that certain chlorothiadiazolyloxyacetamides such as, for example, the compound N-methyl-N-phenyl-2-(3-chloro-1,2,4-thiadiazol-5-yl-oxy)-acetamide have herbicidal properties (cf. EP-A 300344). However, the activity of these prior-art compounds is not entirely satisfactory in all areas of application, in particular at low application rates and concentrations.

This invention, accordingly, provides the novel fluorothiadiazolyloxyacetamides of the general formula (I)

in which
- $R^1$ represents hydrogen or respectively optionally substituted alkyl, alkenyl, alkynyl or arylalkyl,
- $R^2$ represents respectively optionally substituted alkyl, alkoxy, alkenyl, alkenyloxy, alkynyl, cycloalkyl, cycloalkenyl, aryl, arylalkyl or arylalkyloxy, or
- $R^1$ and $R^2$ together with the nitrogen atom that they are attached to form an optionally substituted saturated or unsaturated nitrogen heterocycle which may contain further hetero atoms and to which a benzo grouping may be fused, and
- $R^3$ represents fluorothiadiazolyl.

Additionally, it has been found that the novel fluorothiadiazolyloxyacetamides of the general formula (I) are obtained when alkylsulphonyl compounds of the general formula (II)

in which
- $R^3$ is as defined above and
- R represents alkyl are reacted with hydroxyacetamides of the general formula (III)

in which
- $R^1$ and $R^2$ are each as defined above, if appropriate in the presence of a diluent, if appropriate in the presence of an acid binder and if appropriate in the presence of a catalyst.

Finally, it has been found that the novel fluorothiadiazolyloxyacetamides of the general formula (I) have interesting herbicidal properties.

Surprisingly, the fluorothiadiazolyloxyacetamides of the general formula (I) according to the invention combine partly good crop plant compatibility with a significantly stronger herbicidal activity than the compound N-methyl-N-phenyl-2-(3-chloro-1,2,4-thiadiazol-5-yl-oxy)-acetamide known from the prior art.

The present invention preferably provides compounds of the formula (I) in which
- $R^1$ represents hydrogen, $C_1$–$C_8$-alkyl (which is optionally substituted by fluorine, chlorine, cyano or $C_1$–$C_4$-alkoxy), or $C_2$–$C_8$-alkenyl (which is optionally substituted by fluorine and/or chlorine), or $C_2$–$C_8$-alkynyl or benzyl (which is optionally substituted by fluorine, chlorine, $C_1$–$C_4$-alkyl and/or $C_1$–$C_4$-alkoxy),
- $R^2$ represents $C_1$–$C_8$-alkyl (which is optionally substituted by fluorine, chlorine, cyano or $C_1$–$C_4$-alkoxy), $C_2$–$C_8$-alkenyl (which is optionally substituted by fluorine and/or chlorine), or $C_2$–$C_8$-alkynyl, or $C_3$–$C_6$-cycloalkyl (which is optionally substituted by chlorine and/or $C_1$–$C_3$-alkyl), or C5- or $C_6$-cycloalkenyl, or benzyl (which is optionally substituted by fluorine, chlorine, $C_1$–$C_4$-alkyl and/or $C_1$–$C_{44}$-alkoxy), or phenyl (which is optionally substituted by fluorine, chlorine, bromine, iodine, cyano, nitro, $C_1$–$C_4$-alkyl, trifluoromethyl, $C_1$–$C_4$-alkoxy and/or $C_1$–$C_4$-alkylthio), or $C_1$–$C_8$-alkoxy (which is optionally substituted by $C_1$–$C_4$-alkoxy), or $C_3$–$C_4$-alkenyloxy or benzyloxy, or
- $R^1$ and $R^2$ together with the nitrogen atom that they are attached to form a saturated or unsaturated five- to seven-membered nitrogen heterocycle which is optionally mono- to trisubstituted by $C_1$–$C_3$-alkyl and which is optionally benzo-fused, and
- $R^3$ represents 3-fluoro-1,2,4-thiadiazol-5-yl or 2-fluoro-1,3,4-thiadiazol-5-yl.

The invention in particular provides compounds of the formula (I) in which
- $R^1$ represents methyl, ethyl, n- or i-propyl, n-, i- or s-butyl, n-, i- or s-pentyl (each of which is optionally substituted by fluorine, chlorine, cyano, methoxy or ethoxy), or propenyl, butenyl, propynyl or butynyl,
- $R^2$ represents methyl, ethyl, n- or i-propyl, n-, i- or s-butyl, n-, i- or s-pentyl, n-, i- or s-hexyl (each of which is optionally substituted by fluorine, chlorine, cyano, methoxy or ethoxy), or propenyl, butenyl, pentenyl, propynyl, butynyl or pentynyl, or cyclopentyl or cyclohexyl (each of which is optionally substituted by methyl and/or ethyl), or cyclohexenyl, or benzyl (which is optionally substituted by fluorine, chlorine and/or methyl) or phenyl (which is optionally substituted by fluorine, chlorine, bromine, cyano, nitro, methyl, ethyl, trifluoromethyl, methoxy or ethoxy), or methoxy, ethoxy, n- or i-propoxy, n-, i- or s-butoxy, n-, i- or s-pentyloxy (each of which is optionally substituted by methoxy or ethoxy), or
- $R^1$ and $R^2$ together with the nitrogen atom that they are attached to represent piperidinyl which is optionally mono- to trisubstituted by methyl and/or ethyl, or pyrrolidinyl which is optionally mono- or disubstituted by methyl and/or ethyl, or perhydroazepinyl or 1,2,3,4-tetrahydro(iso)-quinolinyl, and
- $R^3$ represents 3-fluoro-1,2,4-thiadiazol-5-yl.

The radical definitions listed above, whether general or in ranges of preference, apply not only to the end products of the formula (I) but also, correspondingly, to the starting materials and/or intermediates required in each case for the preparation. These radical definitions can be combined with one another as desired, thus including combinations between the preferred ranges indicated.

Examples of the possible meanings of the grouping
in the formula (I) are listed in Table 1 below.
TABLE 1
Examples of the meaning of the grouping
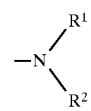
| | |
|---|---|
| —N(CH$_3$)$_2$ | —N(C$_4$H$_9$)$_2$ |
| —N(C$_2$H$_5$)$_2$ | —N(CH$_2$CH=CH$_2$)$_2$ |
| —N(C$_3$H$_7$)$_2$ | —N(CH$_2$C≡CH)$_2$ |
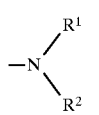
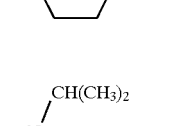
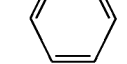
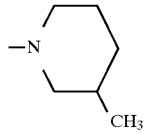
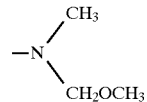
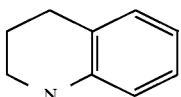
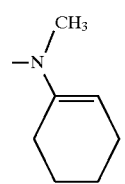
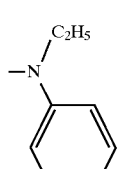
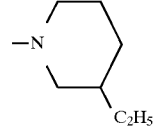
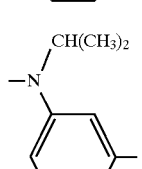
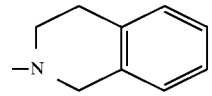
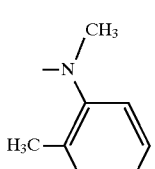
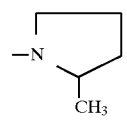
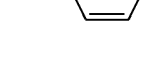

TABLE 1-continued

Examples of the meaning of the grouping (Chemical structures showing various -N(R¹)(R²) groupings, including:
- N-isopropyl-p-tolyl amine
- N-isopropyl-p-methoxyphenyl amine
- N-isopropyl-m-tolyl amine
- N-isopropyl-p-trifluoromethylphenyl amine
- N-methyl-N-ethyl amine
- N-methyl-N-propyl amine
- N-methyl-N-isopropyl amine
- N-methyl-N-butyl amine
- N-methyl-N-isobutyl amine
- N-propyl-N-sec-butyl amine
- N-ethyl-N-propyl amine
- N-ethyl-N-isopropyl amine
- N-ethyl-N-butyl amine
- N-ethyl-N-isobutyl amine
- N-ethyl-N-sec-butyl amine
- N-propyl-N-isopropyl amine And in the right column:
- N-ethyl-cyclohexyl amine
- N-propyl-cyclohexyl amine
- N-isopropyl-cyclohexyl amine
- N-methyl-N-benzyl amine
- N-ethyl-N-benzyl amine
- N-propyl-N-benzyl amine
- N-isopropyl-N-benzyl amine
- N-methyl-N-(4-fluorobenzyl) amine
- N-methyl-N-(4-chlorobenzyl) amine
- N-methyl-N-(3-chlorobenzyl) amine
- N-methyl-N-(2-chlorobenzyl) amine
- N-ethyl-N-(4-fluorobenzyl) amine
- N-isopropyl-N-(4-fluorobenzyl) amine
- N-ethyl-N-(4-chlorobenzyl) amine)

TABLE 1-continued
Examples of the meaning of the grouping
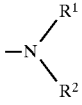
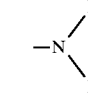
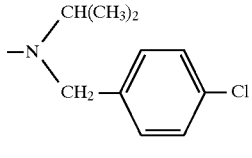
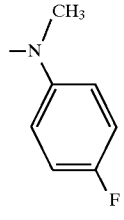
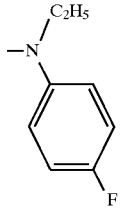
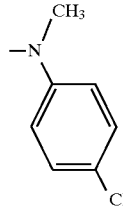
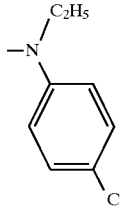
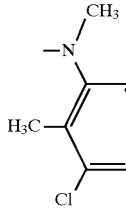
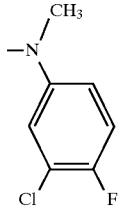
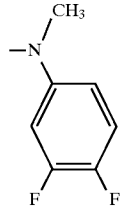
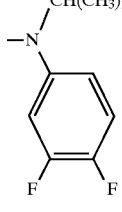
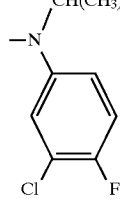
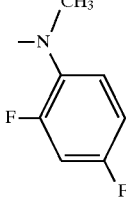
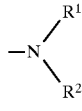
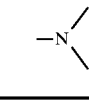
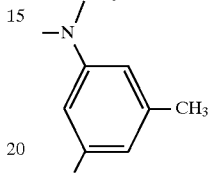
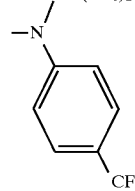
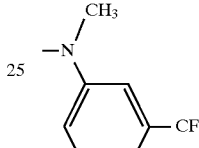
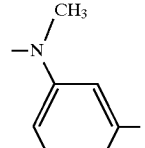
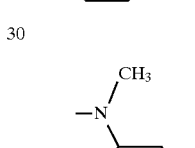
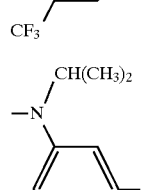
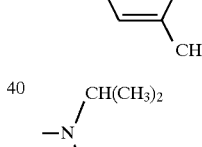
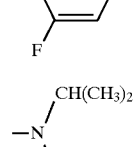
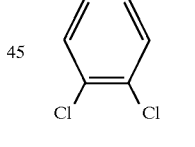
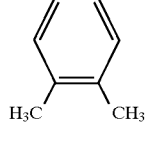
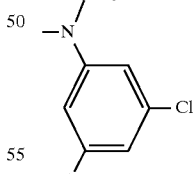
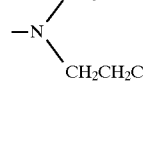
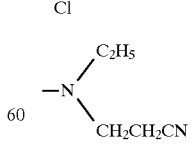
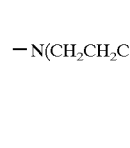

TABLE 1-continued

Examples of the meaning of the grouping

| −N(R¹)(R²) | |
|---|---|
| −N(CH₃)(CH₂CH₂OCH₃) | −N(CH₃)(OC₂H₅) |
| −N(CH₃)(OC₃H₇) | −N(CH₃)(OC₄H₉) |
| −N(C₂H₅)(OC₂H₅) | −N(C₂H₅)(OC₃H₇) |
| −N(C₂H₅)(OC₄H₉) | −N(C₃H₇)(OC₃H₇) |
| −N(C₃H₇)(OC₄H₉) | −N(CH(CH₃)₂)(OC₂H₅) |
| −N(CH(CH₃)₂)(OC₃H₇) | −N(CH(CH₃)₂)(OCH₂CH₂OCH₃) |
| −N(CH₃)(3-Cl-C₆H₄) | −N(CH₃)(4-CH₃-C₆H₄) |
| −N(CH(CH₃)₂)(3-Cl-C₆H₄) | −N(C₃H₇-n)(OCH(CH₃)₂) |
| −N(CH(CH₃)₂)(4-CH₃-C₆H₄) | −N(CH₃)(2-CH₃O-C₆H₄) |
| −N(CH(CH₃)₂)(O−CH(CH₃)₂) | −N(CH(CH₃)₂)(3-CF₃-C₆H₄) |
| 2,6-dimethylmorpholin-4-yl | −N(CH(CH₃)₂)(3,5-Cl₂-C₆H₃) |
| −N(CH₃)(4-OCH₃-C₆H₄) | −N(CH(CH₃)₂)(2-CF₃-C₆H₄) |
| −N(CH₃)(3-OCH₃-C₆H₄) | −N(CH(CH₃)₂)(3,5-(CF₃)₂-C₆H₃) |
| −N(CH(CH₃)₂)(2,5-F₂-C₆H₃) | −N(C₂H₅)(cyclohexyl) |
| −N(CH(CH₃)₂)(3-OCH₃-C₆H₄) | −N(CH₃)(3-CH₃-4-Cl-C₆H₃) |

TABLE 1-continued

Examples of the meaning of the grouping

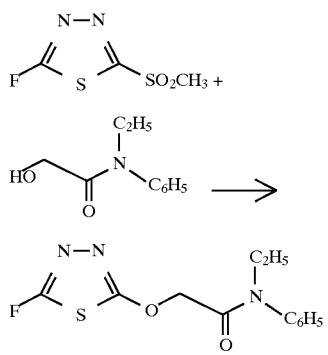

Using, for example, 2-fluoro-5-methylsulphonyl-1,3,4-thiadiazole and N-ethyl-hydroxyacetanilide as starting materials, the course of the reaction of the process according to the invention can be illustrated by the following equation:

a general definition of alkylsulphonyl compounds to be used as starting materials in the process according to the invention for preparing compounds of the general formula (I) is given by the formula (II). In the formula (II), $R^3$ preferably or in particular has that meaning which has already been indicated above, in connection with the description of the compounds of the formula (I), as being preferable or particularly preferable for $R^3$.

The starting materials of the formula (II) have not been disclosed in the literature; as novel substances, they also form part of the subject matter of the present application.

The novel alkylsulphonyl compounds of the general formula (II) are obtained when the corresponding alkylthio compounds of the general formula (IV)

$$R^3\text{—}S\text{—}R \qquad (IV)$$

in which

R and $R^3$ are each as defined above are reacted with an oxidizing agent such as, for example, hydrogen peroxide, if appropriate in the presence of a catalyst such as, for example, sodium tungstate and, if appropriate, in the presence of a diluent such as, for example, acetic acid and/or water, at temperatures between 0° C. and 100° C. (cf. the Preparation Examples).

The alkylthio compounds of the formula (IV) required as intermediates have not been disclosed in the literature; as novel substances, they also form part of the subject matter of the present application.

The novel compounds of the formula (IV) are obtained by reacting the corresponding amino-alkylthio-thiadiazoles with sodium nitrite and hydrogen fluoride in the presence of pyridine at temperatures between −30° C. and +50° C., or by reacting the corresponding chloro-alkylthio-thiadiazoles with potassium fluoride in the presence of a catalyst such as, for example, 18-crown-6 in the presence of a diluent such as, for example, sulpholane at temperatures between 100° C. and 180° C. (cf. the Preparation Examples).

A general definition of the hydroxyacetamides further to be used as starting materials in the process according to the invention for preparing compounds of the general formula (I) is given by the formula (III). In the formula (III), $R^1$ and $R^2$ each preferably or in particular have those meanings which have already been indicated above, in connection with the description of the compounds of the formula (I), as being preferable or particularly preferable for $R^1$ and $R^2$.

The hydroxyacetamides of the formula (III) are known and/or can be prepared by processes known per se (cf. U.S. Pat. No. 4,509,971, U.S. Pat. No. 4,645,525, U.S. Pat. No. 4,334,073, DE 3038598, DE 3038636, EP 37526, EP 348737, DE 3819477).

Suitable diluents for carrying out the process according to the invention are all conventional inert organic solvents. These include in particular aliphatic, alicyclic or aromatic, optionally halogenated hydrocarbons such as, for example, pentane, hexane, heptane, petroleum ether, ligroine, benzine, benzene, toluene, xylene, chlorobenzene, dichlorobenzene, cyclohexane, methylcyclohexane, dichloromethane, chloroform and carbon tetrachloride; ethers, such as diethyl ether, diisopropyl ether, t-butyl methyl ether, t-pentyl methyl ether, dioxane, tetrahydrofuran, ethylene glycol dimethyl ether or ethylene glycol diethyl ether, diethylene glycol dimethyl ether or diethylene glycol diethyl ether; ketones, such as acetone, butanone or methyl isobutyl ketone; nitriles, such as acetonitrile, propionitrile, butyronitrile or benzonitrile; amides, such as N,N-dimethylformamide, N,N-dimethylacetamide, N-methylformanilide, N-methylpyrrolidone or hexamethylphosphoric triamide; esters such as methyl acetate, ethyl acetate, n- or i-propyl acetate, n-, i- or s-butyl acetate, sulphoxides, such as dimethyl sulphoxide; alcohols, such as methanol, ethanol, n- or i-propanol, n-, i-, s- or t-butanol, ethylene glycol monomethyl ether or ethylene glycol monoethyl ether, diethylene glycol monomethyl ether, diethylene glycol monoethyl ether; their mixtures with water or pure water.

The process according to the invention is preferably carried out in the presence of a suitable acid binder. Suitable acid binders are all conventional inorganic or organic bases. These include for example alkali metal or alkaline earth metal hydrides, hydroxides, amides, alkoxides, acetates, carbonates or bicarbonates, such as, for example, lithium hydride, sodium hydride, potassium hydride or calcium hydride, lithium amide, sodium amide or potassium amide, sodium methoxide or potassium methoxide, sodium ethoxide or potassium ethoxide, sodium propoxide or potassium propoxide, aluminium isopropoxide, sodium tert-butoxide or potassium tert-butoxide, sodium hydroxide or potassium hydroxide, ammonium hydroxide, sodium acetate, potassium acetate or calcium acetate, ammonium acetate, sodium carbonate, potassium carbonate or calcium carbonate, ammonium carbonate, sodium bicarbonate or potassium bicarbonate, and basic organic nitrogen compounds, such as trimethylamine, triethylamine, tripropylamine, tributylamine, ethyl diisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl- and 4-methyl-pyridine, 2,4-dimethyl-, 2,6-dimethyl-, 3,4-dimethyl- and 3,5-dimethyl-pyridine, 5-ethyl-2-methyl-pyridine, N-methylpiperidine, N,N-dimethylaminopyridine, diazabicyclooctane (DABCO), diazabicyclononene (DBN) or diazabicycloundecene (DBU).

The reaction temperatures in the practice of the process according to the invention can be varied within a relatively wide range. The process is in general carried out at temperatures of between −50° C. and +100° C., preferably at temperatures between −20° C. and +60° C.

The process according to the invention is generally carried out under atmospheric pressure. However, it is also possible to operate under elevated or reduced pressure—generally between 0.1 bar and 10 bar.

For carrying out the process according to the invention, the starting materials required in each case are in general employed in approximately equimolar quantities. However, it is also possible to use one of the two components employed in each case in a relatively large excess. The reactions are in general carried out in a suitable diluent in the presence of an acid acceptor, and the reaction mixture is stirred for a number of hours at the particular temperature required. Work-up in the process according to the invention is in each case carried out by customary methods (cf. the Preparation Examples).

The active compounds according to the invention can be used as defoliants, desiccants, haulm killers and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum; Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial crops, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective control of weeds in annual crops.

The compounds of the formula (I) according to the invention are particularly suitable for the selective control of monocotyledonous and dicotyledonous weeds in monocotyledonous and dicotyledonous crops, especially pre-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. Suitable liquid solvents are in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:
for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates;

suitable dispersing agents are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, as such or in the form of their formulations, can also be used as mixtures with known herbicides, ready-to-use formulations or tank mixes being possible.

Possible components for the mixtures are known herbicides, for example anilides, such as diflufenican and propanil; arylcarboxylic acids, such as dichloropicolinic acid, dicamba and picloram; aryloxyalkanoic acids, such as 2,4-D, 2,4-DB, 2,4-DP, fluroxypyr, MCPA, MCPP and triclopyr; aryloxy-phenoxy-alkanoic esters, such as diclofop-methyl, fenoxaprop-ethyl, fluazifop-butyl, haloxyfop-methyl and quizalofop-ethyl; azinones, such as chloridazon and norflurazon; carbamates, such as chlorpropham, desmedipham, phenmedipham and propham; chloroacetanilides, such as alachlor, acetochlor, butachlor, metazachlor, metolachlor, pretilachlor and propachlor; dinitroanilines, such as oryzalin, pendimethalin and trifluralin; diphenyl ethers, such as acifluorfen, bifenox, fluoroglycofen, fomesafen, halosafen, lactofen and oxyfluorfen; ureas, such as chlorotoluron, diuron, fluometuron, isoproturon, linuron and methabenzthiazuron; hydroxylamines, such as alloxydim, clethodim, cycloxydim, sethoxydim and tralkoxydim; imidazolinones, such as imazethapyr, imazamethabenz, imazapyr and imazaquin; nitriles, such as bromoxynil, dichlobenil and ioxynil; oxyacetamides, such as mefenacet; sulphonyl-ureas, such as amidosulfuiron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as butylate, cycloate, diallate, EPTC, esprocarb, molinate, prosulfocarb, thiobencarb and triallate; triazines, such as atrazine, cyanazine, simazine, simetryne, terbutryne and terbutylazine; triazinones, such as hexazinone, metamitron and metribuzin; others, such as aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples.

Preparation Examples

EXAMPLE 1

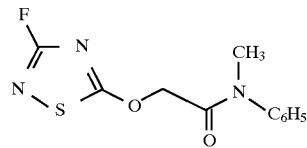

3.6 g (19 mmol) of 3-fluoro-5-methylsulphonyl-1,2,4-thiadiazole and 3.1 g (19 mmol) of N-methyl-N-phenyl-hydroxyacetamide are initially introduced into 30 ml of acetone, and the mixture is cooled to −20° C. A solution of 0.76 g of sodium hydroxide in 3 ml of water is then added dropwise. The reaction mixture is stirred at −15° C. for 12 hours and then diluted with water to about twice the volume, and the crystalline product is isolated by filtration with suction.

2.6 g (52% of theory) of N-methyl-N-phenyl-2-(3-fluoro-1,2,4-thiadiazol-5-yl-oxy)-acetamide of melting point 82° C. are obtained.

By the method of Example 1 and in accordance with the general description of the preparation process according to the invention, it is also possible to prepare, for example, the compounds of the formula (I) listed in Table 2 below, $R^3$ representing in each case 3-fluoro-1,2,4-thiadiazol-5-yl.

TABLE 2

Examples of the compounds of the formula (I)

| Ex. No. | $R^1$ | $R^2$ | Physical data |
|---|---|---|---|
| 2 | | —(CH$_2$)$_6$— | $n_D^{20}$ = 1.5102 |
| 3 | CH$_2$—CH=CH$_2$ | CH$_2$—CH=CH$_2$ | $n_D^{20}$ = 1.5058 |
| 4 | CH(CH$_3$)$_2$ | OCH$_2$CH$_2$OC$_2$H$_5$ | $n_D^{20}$ = 1.4748 |
| 5 | CH(CH$_3$)$_2$ | —C$_6$H$_4$—F | Mp.: 50° C. |
| 6 | | —(CH$_2$)$_4$—CH(C$_2$H$_5$)— | $n_D^{20}$ = 1.5201 |

TABLE 2-continued

Examples of the compounds of the formula (I)

| Ex. No. | R¹ | R² | Physical data |
|---|---|---|---|
| 7 | $CH_3$ | $-CH(CH_3)-C_2H_5$ | $n_D^{20}$ = 1.4949 |
| 8 | n-$C_3H_7$ | n-$C_3H_7$ | $n_D^{20}$ = 1.4945 |
| 9 | | $-(CH_2)_5-$ | |
| 10 | $CH_2-CH=CH_2$ | $CH_2-CH=CH_2$ | |
| 11 | $CH(CH_3)_2$ | $OCH(CH_3)_2$ | $n_D^{20}$ = 1.4808 |
| 12 | $CH_3$ | 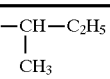 2-methylphenyl | $n_D^{20}$ = 1.5423 |
| 13 | $C_2H_5$ | $C_2H_5$ | $n_D^{20}$ = 1.4983 |
| 14 | $C_2H_5$ | 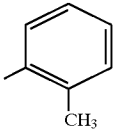 4-fluorophenyl | |
| 15 | | $-(CH_2)_4-CH(CH_3)-$ | $n_D^{20}$ = 1.5292 |
| 16 | | 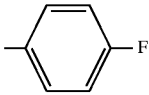 $CH_3-CH(-(CH_2)_3-n-C_4H_9)$ | $n_D^{20}$ = 1.5173 |
| 17 | $CH_3$ | n-$C_4H_9$ | $n_D^{20}$ = 1.4960 |
| 18 | $CH_3$ | 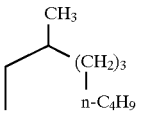 2-chlorophenyl | |
| 19 | $C_2H_5$ | $C_6H_5$ | |
| 20 | n-$C_4H_9$ | n-$C_4H_9$ | $n_D^{20}$ = 1.4941 |
| 21 | $CH_3$ | 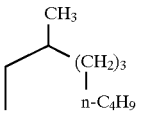 3-(trifluoromethyl)phenyl | Mp.: 48° C. |
| 22 | $CH_3$ | 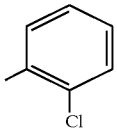 $(CH_3)_2CH-CH(C_2H_5)(CH_3)$ | $n_D^{20}$ = 1.4867 |
| 23 | 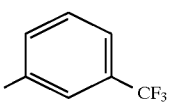 | $OCH_3$ | |
| 24 | $CH_3$ | 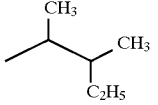 cyclopentenyl | |
| 25 | $CH_3$ | 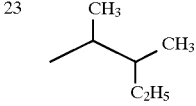 4-fluorophenyl | |
| 26 | $CH_2CH_2OC_2H_5$ | $CH_2CH_2OC_2H_5$ | |

TABLE 2-continued

Examples of the compounds of the formula (I)

| Ex. No. | R$^1$ | R$^2$ | Physical data |
|---|---|---|---|
| 27 | | —CH$_2$—CH(CH$_3$)—CH$_2$—CH(CH$_3$)—CH$_2$— | |
| 28 | CH$_3$ | CH$_2$C$_6$H$_5$ | |
| 29 | CH$_3$ | cyclohexenyl | $n_D^{20}$ = 1.5278 |
| 30 | CH$_3$ | CH$_2$CH$_2$C≡CH | |
| 31 | CH(CH$_3$)$_2$ | 2-methylphenyl | |
| 32 | CH$_3$ | 2,3-dimethylphenyl | |
| 33 | | —(CH$_2$)$_2$—CH(CH$_3$)—(CH$_2$)$_2$— | $n_D^{20}$ = 1.5191 |
| 34 | C$_2$H$_5$ | phenyl | Mp.: 40° C. |
| 35 | | —(CH$_2$)$_3$—(2-methylphenyl) | $n_D^{20}$ = 1.5870 |
| 36 | | —(CH$_2$)$_2$—CH(CH$_3$)—CH$_2$—CH(CH$_3$)— | $n_D^{20}$ = 1.5105 |
| 37 | | —(CH$_2$)$_3$—CH(C$_2$H$_5$)—CH$_2$— | $n_D^{20}$ = 1.5136 |
| 38 | CH(CH$_3$)$_2$ | 3-(trifluoromethyl)phenyl | Mp.: 40° C. |
| 39 | CH(CH$_3$)$_2$ | cyclohexadienyl | $n_D^{20}$ = 1.5212 |
| 40 | CH(CH$_3$)$_2$ | 3-methoxyphenyl | Mp.: 85° C. |

Starting materials of the formula (II)

EXAMPLE (II-1)

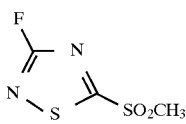

A mixture of 22.3 g (0.15 mol) of 3-fluoro-5-methylthio-1,2,4-thiadiazole, 0.3 g of sodium tungstate and 120 ml of acetic acid is heated to 70° C., and 48 ml (0.44 mol H$_2$O$_2$) of an aqueous solution of hydrogen peroxide are added dropwise at this temperature. The mixture is then diluted with 400 ml of water and extracted with chloroform. The organic phase is then separated off, washed with 5% strength aqueous sodium hydrogen sulphite solution, dried with sodium sulphate and filtered. The solvent is then carefully distilled off from the filtrate under water pump vacuum.

20 g (77% of theory) of 3-fluoro-5-methylsulphonyl-1,2,4-thiadiazole are obtained as a pale-yellow oily residue having a refractive index n$^{20}_D$=1.5430.

EXAMPLE (II-2)

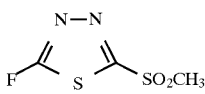

15 g (0.10 mol) of 2-fluoro-5-methylthio-1,3,4-thiadiazole are dissolved in 50 ml of acetic acid and, at an internal temperature of from 10° C. to 15° C., a solution of 26.5 g (0.17 mol) of potassium permanganate in 400 ml of water is added dropwise. The reaction mixture is subsequently stirred for about 60 minutes at about 1° C., and saturated aqueous sodium hydrogen sulphite solution is then added dropwise until decolorization occurs. The crystalline product is then isolated by filtration with suction.

15.9 g (59% of theory) of 2-fluoro-5-methylsulphonyl-1,3,4-thiadiazole of melting point 65° C. are obtained.
Starting materials of the formula (IV)

EXAMPLE (IV-1)

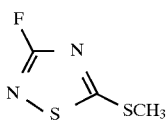

1240 ml (61.2 mol) of hydrogen fluoride are initially charged at 0° C. to 10° C. and, with cooling, admixed with 660 ml (8.14 mol) of pyridine. At 10° C., 100 g (0.68 mol) of 3-amino-5-methylthio-1,2,4-thiadiazole are then added and the mixture is subsequently cooled to −15° C. At −15° C. to −5° C., 49.2 g (0.72 mol) of sodium nitrite are then added a little at a time over a period of about 3 hours. The temperature of the mixture is then slowly raised from about −10° C. to +40° C., whereupon nitrogen is liberated. After the formation of nitrogen has ceased, the mixture is poured into 2.5 liters of water and then extracted four times with 250 ml of cyclohexane each time. The combined extracts are washed with aqueous sodium bicarbonate solution, dried with sodium sulphate and filtered. The filtrate is concentrated under water pump vacuum and the residue is fractionally distilled over a Vigreux column (10 cm) under high vacuum.

34 g (33% of theory) of 3-fluoro-5-methylthio-1,2,4-thiadiazole of boiling point 62° C./0.3 mbar are obtained.

$^1$H NMR (CDCl$_3$, δ): 2.73 ppm.

EXAMPLE (IV-2)

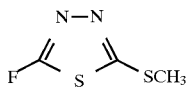

63 g of 2-chloro-5-methylthio-1,3,4-thiadiazole (94% pure, 0.356 mol) together with 45 g of potassium fluoride and 1 g of 18-crown-6 are dissolved in 136 g of sulpholane, and the mixture is heated at 145° C. for 4 hours. A quick vacuum distillation of the reaction mixture yields 40 g of crude product (about 85% purity), from which 30 g (55% of theory) of 2-fluoro-5-methylthio-1,3,4-thiadiazole of boiling point 73° C.–75° C./1 mbar are isolated by fractional vacuum distillation.

Use Examples

In the Use Examples, the compound mentioned below is employed as comparison substance.

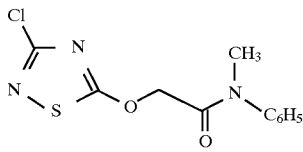

N-Methyl-N-phenyl-2-(3-chloro-1,2,4-thiadiazol-5-yl-oxy)-acetamide (known from EP-A 300344).

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is watered with the preparation of the active compound. It is advantageous to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control.

The figures denote:

0%=no action (like untreated control)

100%=total destruction

In this test, the compounds according to Preparation Examples 1, 2, 3 and 4, for example, exhibit a significantly stronger activity against weeds than the known compound A, while some of them are well tolerated by crops, such as, for example, barley and soyabeans.

TABLE A

| | | Pre-emergence test/greenhouse | | | | | | | |
|---|---|---|---|---|---|---|---|---|---|
| Active compound | Application rate (g/ha) | Barley | Soja bean | Agropyron | Avena | Bromus | Amaranthus | Matricaria | Solanum |
| (A) (known) | 500 | 40 | 40 | 60 | 60 | 40 | 70 | 70 | 20 |
| (1) | 500 | 20 | 20 | 95 | 95 | 95 | 100 | 100 | 95 |
| (2) | 500 | 0 | 95 | 90 | 70 | 100 | 95 | 95 | |
| (3) | 500 | — | 0 | 100 | 100 | 95 | 100 | 90 | 80 |
| (4) | 500 | — | 60 | 100 | 100 | 100 | 100 | 90 | 70 |

We claim:

1. A fluorothiadiazolyloxyacetamide compound of the formula (I)

in which

R$^1$ represents hydrogen, C$_1$–C$_8$-alkyl (which is optionally substituted by fluorine, chlorine, cyano or C$_1$–C$_4$-alkoxy), C$_2$–C$_8$-alkenyl (which is optionally substituted by fluorine and/or chlorine), or C$_2$–C$_8$-alkynyl or benzyl (which is optionally substituted by fluorine, chlorine, C$_1$–C$_3$-alkyl and/or C$_1$–C$_4$-alkoxy), R$^2$ represents C$_1$–C$_8$-alkyl (which is optionally substituted by fluorine, chlorine, cyano or C$_1$–C$_4$-alkoxy), C$_2$–C$_8$-alkenyl (which is optionally substituted by fluorine and/or chlorine), or C$_2$–C$_8$-alkynyl, or C$_3$–C$_6$-cycloalkyl (which is optionally substituted by chlorine and/or C$_1$–C$_3$-alkyl), or C$_5$- or C$_6$-cycloalkenyl, or benzyl (which is optionally substituted by fluorine, chlorine, C$_1$–C$_4$-alkyl and/or C$_1$–C$_4$-alkoxy), or phenyl (which is optionally substituted by fluorine, chlorine, bromine, iodine, cyano, nitro, C$_1$–C$_4$-alkyl, trifluoromethyl, C$_1$–C$_4$-alkoxy and/or C$_1$–C$_4$-alkylthio), or C$_1$–C$_8$-alkoxy (which is optionally substituted by C$_1$–C$_4$-alkoxy), or C$_3$–C$_4$-alkenyloxy or benzyloxy, or R$^1$ and R$^2$ together with the nitrogen atom that they are attached to form a saturated or unsaturated five- to seven-membered nitrogen heterocycle which is optionally mono- to trisubstituted by C$_1$–C$_3$-alkyl and which is optionally benzo-fused, and R$^3$ represents 3-fluoro-1,2,4-thiadiazol-5-yl.

2. Compounds of the formula (I) according to claim 1, wherein

R$^1$ represents methyl, ethyl, n- or i-propyl, n-, i- or s-butyl, n-, i- or s-pentyl (each of which is optionally substituted by fluorine, chlorine, cyano, methoxy or ethoxy), or propenyl, butenyl, propynyl or butynyl, $R^2$ represents methyl, ethyl, n- or i-propyl, n-, i- or s-butyl, n-, i- or s-pentyl, n-, i- or s-hexyl (each of which is optionally substituted by fluorine, chlorine, cyano, methoxy or ethoxy), or propenyl, butenyl, pentenyl, propynyl, butynyl or pentynyl, or cyclopentyl or cyclohexyl (each of which is optionally substituted by methyl and/or ethyl), or cyclohexenyl, or benzyl (which is optionally substituted by fluorine, chlorine and/or methyl) or phenyl (which is optionally substituted by fluorine, chlorine, bromine, cyano, nitro, methyl, ethyl, trifluoromethyl, methoxy or ethoxy), or methoxy, ethoxy, n- or i-propoxy, n-, i- or s-butoxy, n-, i- or s-pentyloxy (each of which is optionally substituted by methoxy or ethoxy), or $R^1$ and $R^2$ together with the nitrogen atom that they are attached to represent piperidinyl which is optionally mono- to trisubstituted by methyl and/or ethyl, or pyrrolidinyl which is optionally mono- or disubstituted by methyl and/or ethyl, or perhydroazepinyl or 1,2,3,4-tetrahydro(iso)-quinolinyl, and $R^3$ represents 3-fluoro-1,2,4-thiadiazol-5-yl.

3. An herbicidal composition comprising an herbicidally effective amount of a compound according to claim 1 and a diluent.

4. A method of combating unwanted vegetation which comprises administering to such vegetation or to a locus from which it is desired to exclude such vegetation an herbicidally effective amount of a compound according to claim 1.

* * * * *

UNITED STATES PATENT AND TRADEMARK OFFICE
CERTIFICATE OF CORRECTION

PATENT NO. : 5,858,922
DATED : January 12, 1999
INVENTOR(S) : Forster, et al.

It is certified that error appears in the above-identified patent and that said Letters Patent is hereby corrected as shown below:

Col. 23, line 60   After " alkoxy), " insert -- or --

Signed and Sealed this

Twelfth Day of October, 1999

Attest:

Q. TODD DICKINSON

Attesting Officer      Acting Commissioner of Patents and Trademarks